United States Patent
Watakabe

(10) Patent No.: US 10,604,461 B2
(45) Date of Patent: Mar. 31, 2020

(54) METHOD FOR PRODUCING FLUORINE-CONTAINING COMPOUND HAVING IODINE ATOM CONTENT REDUCED

(71) Applicant: AGC Inc., Chiyoda-ku (JP)

(72) Inventor: Atsushi Watakabe, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 15 days.

(21) Appl. No.: 15/943,750

(22) Filed: Apr. 3, 2018

(65) Prior Publication Data

US 2018/0222828 A1    Aug. 9, 2018

Related U.S. Application Data

(63) Continuation of application No. PCT/JP2016/084325, filed on Nov. 18, 2016.

(30) Foreign Application Priority Data

Nov. 20, 2015 (JP) .................. 2015-227178

(51) Int. Cl.
| | |
|---|---|
| C07C 17/23 | (2006.01) |
| C08F 8/26 | (2006.01) |
| C07C 41/24 | (2006.01) |
| C07C 23/08 | (2006.01) |
| C07C 23/10 | (2006.01) |
| C08F 14/02 | (2006.01) |
| C08F 14/18 | (2006.01) |

(52) U.S. Cl.
CPC .............. *C07C 17/23* (2013.01); *C07C 23/08* (2013.01); *C07C 23/10* (2013.01); *C07C 41/24* (2013.01); *C08F 8/26* (2013.01); *C08F 14/02* (2013.01); *C08F 14/18* (2013.01)

(58) Field of Classification Search
CPC ...................................... C07C 17/23
See application file for complete search history.

(56) References Cited

U.S. PATENT DOCUMENTS

| | | | |
|---|---|---|---|
| 5,917,074 A | 6/1999 | Hammond et al. | |
| 7,030,194 B1 | 4/2006 | Nakagawa et al. | |
| 8,357,772 B2 * | 1/2013 | Horiuti ................. | C07C 17/278 526/249 |
| 2003/0032847 A1 | 2/2003 | Reynolds | |
| 2006/0270570 A1 * | 11/2006 | Grottenmueller ........ | C09G 3/00 508/582 |
| 2009/0105435 A1 * | 4/2009 | Hung .................... | C08F 214/18 526/243 |

FOREIGN PATENT DOCUMENTS

| | | |
|---|---|---|
| GB | 1364495 | * 12/1971 |
| JP | 57-94004 | 6/1982 |
| JP | 4-202303 | 7/1992 |
| JP | 9-291062 | 11/1997 |
| JP | 2000-327713 | 11/2000 |
| JP | 2000-344831 | 12/2000 |
| JP | 2004-532918 | 10/2004 |
| WO | WO99/08709 | 2/1999 |
| WO | WO 99/18138 | 4/1999 |
| WO | WO 2006/090728 A1 | 8/2006 |

OTHER PUBLICATIONS

Polymer Properties Database (2015) (Year: 2015).*
Zhang, Journal of Fluorine Chemistry, 130 (2009) p. 671-673 (Year: 2009).*
Howell, Journal of Fluorine Chemistry, 72 (1995) p. 61-68 (Year: 1995).*
Dolbier, Journal of Fluorine Chemistry, 72 (1995) p. 235-240 (Year: 1995).*
International Search Report dated Jan. 24, 2017 in PCT/JP2016/084325, filed on Nov. 18, 2016.

* cited by examiner

*Primary Examiner* — Robert C Boyle
(74) *Attorney, Agent, or Firm* — Oblon, McClelland, Maier & Neustadt, L.L.P.

(57) ABSTRACT

The purpose of the present invention is to obtain a fluorine-containing compound which is easily stabilized without irradiation of ultraviolet light, by efficiently converting a C—I bond in an iodine-containing compound having a group represented by —CFRf—I (wherein Rf is a fluorine atom or a perfluoroalkyl group) to a C—H bond. A method for producing a fluorine-containing compound having an iodine atom content reduced than the following iodine-containing compound, which comprises subjecting an iodine-containing compound having a group represented by —CFRf—I (wherein Rf is a fluorine atom or a perfluoroalkyl group) to deiodinating treatment in the presence of an organic peroxide and a hydrogen-containing compound having a group represented by —CHR$^1$—CHR$^2$—CHR$^3$— (wherein R$^1$, R$^2$ and R$^3$ are each independently a hydrogen atom or an alkyl group).

12 Claims, No Drawings

METHOD FOR PRODUCING FLUORINE-CONTAINING COMPOUND HAVING IODINE ATOM CONTENT REDUCED

TECHNICAL FIELD

The present invention relates to a method for producing a fluorine-containing compound stabilized by reducing iodine atoms remaining in the fluorine-containing compound.

BACKGROUND ART

There is a method of synthesizing a polymer by cleaving a carbon-iodine bond in a compound having iodine atoms, and radically polymerizing by the resulting carbon radical, a radical polymerizable monomer (Patent Document 1). However, if iodine atoms remain in the obtained polymer, iodine is likely to be easily liberated, and due to light or heat, degradation or coloration of the polymer may occur.

To prevent such a phenomenon, a method of treating the polymer having iodine atoms remained, by light, heat or a radical initiator in the presence of isopentane, toluene, carbon tetrachloride, etc., to convert the C—I bond in the polymer to a C—H bond or C—Cl bond, is disclosed (Patent Document 1).

In Example 9 in Patent Document 1, it is disclosed that iodine was almost completely removed by dissolving the polymer having iodine atoms remained, in isopentane and R-113, and adding sodium sulfite, followed by ultraviolet irradiation. The polymer having iodine atoms remained, subjected to the treatment, had —CH$_2$CH(COOCH$_3$)—I and —CH$_2$CH(C$_4$H$_3$)—I, as carbon atom-iodine atom bonds, but it was not one having —CF$_2$—I.

PRIOR ART DOCUMENT

Patent Document

Patent Document 1: JP-A-4-202303

DISCLOSURE OF INVENTION

Technical Problem

In the prior art, there was no disclosure of a method for efficiently converting a C—I bond in an iodine-containing compound having a group represented by —CFRf—I (Rf is a fluorine atom or a perfluoroalkyl group), to a C—H bond.

It is an object of the present invention to obtain a stabilized fluorine-containing compound easily without using an equipment for ultraviolet radiation, by efficiently converting a C—I bond in an iodine-containing compound having a group represented by —CFRf—I (Rf is a fluorine atom or a perfluoroalkyl group) to a C—H bond.

Solution to Problem

The present invention provides a method for producing a fluorine-containing compound, which has the following construction [1].

[1] A method for producing a fluorine-containing compound having an iodine atom content reduced than the following iodine-containing compound, which comprises subjecting an iodine-containing compound having a group represented by the following formula (1i) or a group represented by the following formula (2i), to deiodinating treatment in the presence of an organic peroxide and a hydrogen-containing compound having a group represented by the following formula (3):

in the formula (1i), Rf is a fluorine atom or a perfluoroalkyl group, in the formula (2i), the ring containing Rf' is a 5- or 6-membered ring, Rf' is a perfluoroalkylene group having a linear or branched structure, which may have an etheric oxygen atom, and R$^a$ and R$^b$ are each independently a fluorine atom, a C$_{1-5}$ perfluoroalkyl group or a C$_{1-5}$ perfluoroalkoxy group, and in the formula (3), R$^1$, R$^2$ and R$^3$ are each independently a hydrogen atom or an alkyl group.

Advantageous Effects of Invention

By the present invention, it is possible to efficiently convert a C—I bond in the fluorine-containing compound having a group represented by —CFRf—I (Rf is a fluorine atom or a perfluoroalkyl group) to a C—H bond, and to easily obtain a stabilized fluorine-containing compound.

DESCRIPTION OF EMBODIMENTS

The following expressions and definitions of terms apply throughout this specification including claims, unless otherwise stated.

A structural unit represented by the formula (m1) will be referred to as a unit (m1). Units represented by other formulae will be referred to in the same manner.

A monomer represented by the formula (m1) will be referred to as a monomer (m1). Compounds represented by other formulae will be referred to in the same manner.

A group represented by the formula (1i) will be referred to as a group (1i). Groups represented by other formulae will be referred to in the same manner.

A "unit" means a unit derived from a monomer and formed by radical polymerization of the monomer. A unit may be a unit formed directly by a polymerization reaction, or may be a unit having a part of such a unit converted to another structure by treating the polymer.

A "fluorine-containing compound" means a compound having a fluorine atom bonded to a carbon atom.

An "iodine-containing compound" means a compound having an iodine atom bonded to a carbon atom.

A "hydrogen-containing compound" means a compound having a hydrogen atom bonded to a carbon atom.

A "perfluoroalkyl group" means a group having all of hydrogen atoms in an alkyl group substituted by fluorine atoms. A "perfluoroalkylene group" means a group having all of hydrogen atoms in an alkylene group substituted by fluorine atoms.

A "polyfluoroalkyl group" means a group having some of hydrogen atoms in an alkyl group substituted by fluorine atoms. A "polyfluoroalkylene group" means a group having some of hydrogen atoms in an alkylene group substituted by fluorine atoms.

The "deiodinating treatment" means a treatment for converting a C—I bond in a compound to a C—H bond.

A "chain transfer agent" is meant for a compound which provides a hydrogen atom to a radical formed by having an iodine atom withdrawn.

(Iodine-Containing Compound)

The object to be treated by deiodinating treatment in the present invention is an iodine-containing compound having a group (1i) or group (2i). That is, the iodine-containing compound is a compound to be treated in the present invention, but the compound to be treated can be regarded as a fluorine-containing compound, since it contains fluorine.

—CFRf—I    Formula (1i)

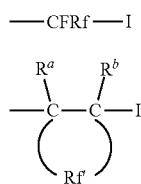    Formula (2i)

In the formula (1i), Rf is a fluorine atom or a perfluoroalkyl group.

The perfluoroalkyl group may be linear or branched and is preferably linear.

The number of carbon atoms in the perfluoroalkyl group is preferably from 1 to 6, more preferably from 1 to 4.

Rf is preferably a fluorine atom, a trifluoromethyl group or a pentafluoroethyl group, more preferably a fluorine atom or a trifluoromethyl group, further preferably a fluorine atom.

In the formula (2i), the ring containing Rf' is a 5- or 6-membered ring, and Rf' is a perfluoroalkylene group having a linear or branched structure, which may have an etheric oxygen atom. The ring containing Rf' is preferably a 5-membered ring. Rf' is preferably one having a branched structure, more preferably one containing an etheric oxygen atom.

$R^a$ and $R^b$ are each independently a fluorine atom, a $C_{1-5}$ perfluoroalkyl group, or a $C_{1-5}$ perfluoroalkoxy group. At least one of $R^a$ and $R^b$ is preferably a fluorine atom, and more preferably, both are fluorine atoms.

The perfluoroalkyl group and the perfluoroalkoxy group may be linear or branched, and are preferably linear.

The iodine-containing compound in the present invention may be a low molecular compound or a polymer compound.

When the iodine-containing compound is a low molecular compound, as such a low molecular compound, a compound represented by the following formula (4) or a compound represented by the following formula (5) may be mentioned.

$Q^1$-CFRf—I    Formula (4)

$Q^2$-(CFRf—I)$_2$    Formula (5)

In the formula (4), Rf is a fluorine atom or a perfluoroalkyl group, and $Q^1$ is a fluorine atom or a polyfluoroalkyl group which may have an etheric oxygen atom. In the formula (5), Rf are each independently a fluorine atom or a perfluoroalkyl group, and $Q^2$ is a polyfluoroalkylene group which may have an etheric oxygen atom.

Preferred embodiments of Rf are as described in the formula (1i).

When $Q^1$ is a polyfluoroalkyl group having an etheric oxygen atom, the number of the oxygen atoms may be one or may be two or more. Further, such an oxygen atom may be inserted between carbon-carbon atoms in the polyfluoroalkyl group, or it may be present at the terminal on the bonding side of the group (1i). The polyfluoroalkyl group may be linear or branched and is preferably linear. The number of carbon atoms in the polyfluoroalkyl group is preferably from 1 to 20, more preferably from 1 to 10. The polyfluoroalkyl group is preferably a perfluoroalkyl group.

When $Q^2$ is a polyfluoroalkylene group having an etheric oxygen atom, the number of the oxygen atoms may be one or may be two or more. Further, such an oxygen atom may be inserted between carbon-carbon atoms in the polyfluoroalkylene group, or may be present at the terminal on the bonding side of the group (1i). The polyfluoroalkylene group may be linear or branched and is preferably linear. The number of carbon atoms in the polyfluoroalkylene group is preferably from 1 to 20, more preferably from 1 to 10. The polyfluoroalkylene group is preferably a perfluoroalkylene group.

When the iodine-containing compound is a polymer compound, as such a polymer compound, a polymer obtained by a radical polymerization reaction of a monomer may be mentioned. It is preferably a polymer having at least one C—I bond, in which all of hydrogen atoms bonded to carbon atoms are substituted by fluorine atoms. The higher the proportion of fluorine atoms in the polymer, the better the properties such as heat resistance, light resistance, chemical stability, low refractive index, low dielectric constant, water/oil repellency of the polymer after deiodinating treatment. The polymer may be a branched polymer having a branched molecular chain, or may be an amorphous branched polymer.

The amorphous branched polymer may, for example, be a polymer comprising units (m1) based on a monomer (m1) having an iodine atom, and units (m2) based on either one or both of a monomer (m2) having an alicyclic structure and a monomer (m2') capable of forming an alicyclic structure by cyclopolymerization.

The branching point of the branched polymer is made of a unit having an iodine atom withdrawn from a unit (m1). The unit (m1) having an iodine atom withdrawn by a radical in the polymerization reaction system during formation of the branched polymer, becomes the starting point for polymerization of the monomer component and becomes a branching point of the polymer formed after polymerization of the monomer component.

There may be a case where a group (1i) in the branched polymer is made of an iodine atom (remaining without being withdrawn during the polymerization) in the unit (m1). Further, a group (1 i) in the branched polymer may be present as a portion having an iodine atom bonded to a unit (m2) i.e. as a polymer terminal portion having an iodine atom bonded. Such an iodine atom present at a polymer terminal portion is an iodine atom detached from a unit (m1), or an iodine atom which has been moved from a monomer (m1) having iodine in the polymerization reaction system.

Monomer (m1):

A monomer (m1) is a monomer having an iodine atom. As such a monomer (m1), in order to increase the proportion of fluorine atoms in a polymer to be produced, preferred is a monomer wherein some of the hydrogen atoms bonded to carbon atoms are substituted by iodine atoms, and all of the remaining hydrogen atoms are substituted by fluorine atoms.

As the monomer (m1), the following monomers may be mentioned.

CF$_2$=CFOCF$_2$ CF(CF$_3$)OCF$_2$ CF$_2$—I,
CF$_2$=CFOCF$_2$ CF(CF$_3$)OCF$_2$ CF(CF$_3$)OCF$_2$ CF$_2$—I,
CF$_2$=CFO(CF$_2$—I, CF$_2$=CFO(CF$_2$)$_3$—I,
CF$_2$=CFO(CF$_2$—I, CF$_2$=CFO(CF$_2$)$_5$—I,
CF$_2$=CFO(CF$_2$—I, CF$_2$=CFO(CF$_2$)$_8$—I,
CF$_2$=CFOCF$_2$ CF(CF$_3$)—I,
CF$_2$=CFOCF$_2$ CF(CF$_3$)OCF$_2$ CF(CF$_3$)—I,
CF$_2$=CFO(CF$_2$)$_3$OCF$_2$ CF$_2$—I,
CF$_2$=CFOCF$_2$ CF$_2$OCF$_2$CF$_2$CF$_2$—I,
CF$_2$=CFOCF(CF$_3$)CF$_2$OCF$_2$ CF$_2$—I,
CF$_2$=CFOCF$_2$CF$_2$CH$_2$—I,
CF$_2$=CFOCF$_2$ CF(CF$_3$)OCF$_2$CF$_2$CH$_2$—I,
CF$_2$=CFOCF$_2$CF$_2$CH$_2$CH$_2$CH$_2$—I,
CH$_2$=CHCF$_2$ CF$_2$—I, CH$_2$=CHCF$_2$CF$_2$CF$_2$ CF$_2$—I,
CH$_2$=CFCF$_2$CF$_2$—I, CH$_2$=CFCF$_2$CF$_2$CF$_2$ CF$_2$—I,
CH$_2$=CFCF$_2$OCF(CF$_3$)—I,
CH$_2$=CFCF$_2$OCF(CF$_3$)CF$_2$OCF(CF$_3$)—I,
CH$_2$=CFCF$_2$OCF(CF$_3$)CF$_2$OCF(CF$_3$)CF$_2$OCF(CF$_3$)—I.

Among these, a monomer containing a group (1i) is preferred, since stabilization of the polymer to be produced is easy. A perfluoromonomer is more preferred.

Monomer (m2):

A monomer (m2) is a monomer having an alicyclic structure.

The alicyclic structure is a cyclic organic group which may have one or two etheric oxygen atoms, wherein hydrogen atoms bonded to carbon atoms may be substituted by fluorine atoms.

As the monomer (m2), in order to increase the proportion of fluorine atoms in the polymer to be formed, a perfluoromonomer is preferred.

The polymerizable carbon-carbon double bond in the monomer (m2) may be constituted by adjacent two carbon atoms constituting the alicyclic structure, or may be constituted by one carbon atom constituting the alicyclic structure and one carbon atom which is present adjacent thereto outside the alicyclic structure.

As the monomer (m2), for example, a monomer (m20) or a monomer (m22) may be mentioned, and the monomer (m20) is preferred. By copolymerizing the monomer (m20) and the monomer (m1), a branched polymer having a group (2i) at the terminal is obtainable. It is further preferred that the monomer (m20) is a monomer (m21).

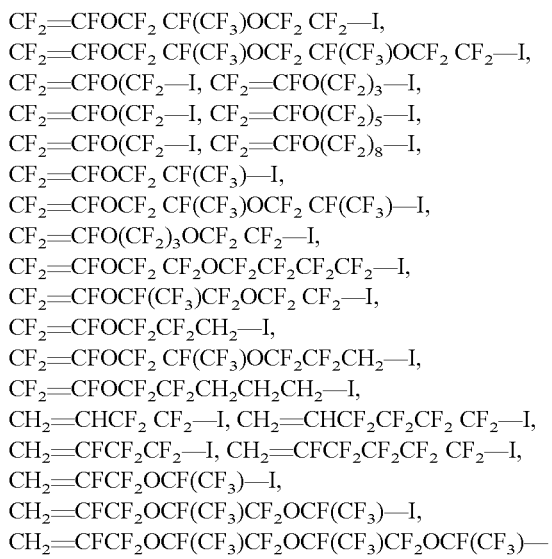

(m20)

(m22)

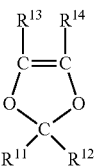

(m21)

In the formula (m20), Rf, R$^a$ and R$^b$ are the same as in the formula (2i).

In the formula (m21), R$^{11}$ and R$^{12}$ are each independently a fluorine atom or a C$_{1-5}$ perfluoroalkyl group.

R$^{13}$ and R$^{14}$ are each independently a fluorine atom, a C$_{1-5}$ perfluoroalkyl group or a C$_{1-5}$ perfluoroalkoxy group. From the viewpoint of high polymerization reactivity, it is preferred that at least one of R$^{13}$ and R$^{14}$ is a fluorine atom, and it is more preferred that both are fluorine atoms.

The perfluoroalkyl group and the perfluoroalkoxy group may be linear or branched, and is preferably linear.

In the formula (m22), R$^{21}$ to R$^{26}$ are each independently a monovalent perfluoro-organic group which may have an etheric oxygen atom, or a fluorine atom. As the monovalent perfluoro-organic group, a perfluoroalkyl group is preferred. In a case where the perfluoroalkyl group has an etheric oxygen atom, the number of the oxygen atoms may be one or may be two or more. Further, such an oxygen atom may be inserted between carbon-carbon atoms in the perfluoroalkyl group, or it may be present at the terminal on the side bonded to a carbon atom. The perfluoroalkyl group may be linear or branched and is preferably linear.

From the viewpoint of high polymerization reactivity, it is preferred that at least one of R$^{25}$ and R$^{26}$ is a fluorine atom, and it is more preferred that both are fluorine atoms.

As the monomer (m21), for example, monomers (m21-1) to (m21-7) may be mentioned.

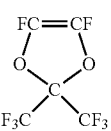

(m21-1)

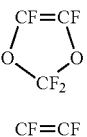

(m21-2)

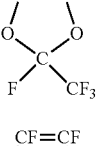

(m21-3)

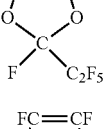

(m21-4)

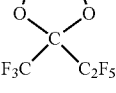

(m21-5)

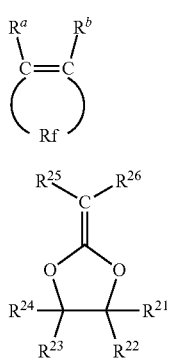

-continued (m21-6)

$$\underset{F_3C}{\overset{FC=CF}{\underset{O}{\bigvee}}}\underset{C_5F_{11}}{\overset{O}{\bigvee}}$$

(m21-7)

$$\underset{O}{\overset{CF=C}{\underset{CF_2}{\bigvee}}}\overset{OCF_3}{\bigvee}$$

As the monomer (m22), for example, a monomer (m22-1) or a monomer (m22-2) may be mentioned. From the viewpoint of easy synthesis, the monomer (m22-1) is more preferred.

(m22-1)

$$\underset{F_2C-CF-CF_3}{\overset{CF_2}{\underset{O}{\bigvee}}\overset{O}{\bigvee}}$$

(m22-2)

$$\underset{F_2C-CF-CF_2CF_2CF_2CF_3}{\overset{CF_2}{\underset{O}{\bigvee}}\overset{O}{\bigvee}}$$

Monomer (m2'):

A monomer (m2') is a monomer capable of forming an alicyclic structure by cyclopolymerization.

The alicyclic structure is a cyclic organic group which may have one or two etheric oxygen atoms, wherein hydrogen atoms bonded to carbon atoms may be substituted by fluorine atoms.

As the monomer (m2'), from the viewpoint of durability, a perfluoromonomer is preferred, and, for example, a monomer (m24) may be mentioned.

$$CF(R^{41})=C(R^{43})-O-CF(R^{46})-CF(R^{45})-C(R^{44})=CF(R^{42})$$ (m24).

$R^{41}$ to $R^{46}$ are each independently a monovalent perfluoro-organic group which may have an etheric oxygen atom, or a fluorine atom. As the monovalent perfluoro-organic group, a perfluoroalkyl group is preferred. In a case where the perfluoroalkyl group has an etheric oxygen atom, the number of oxygen atoms may be one or may be two or more. Further, such an oxygen atom may be inserted between carbon-carbon atoms in the perfluoroalkyl group, or it may be present at the terminal on the side bonded to a carbon atom. The perfluoroalkyl group may be linear or branched and is preferably linear.

$R^{41}$ to $R^{44}$ are, from the viewpoint of high polymerizability, more preferably fluorine atoms.

As the monomer (m24), for example, monomers (m24-1) to (m24-3) may be mentioned, and from the viewpoint of efficiency in the monomer synthesis, the monomer (m24-1) is preferred.

$$CF_2=CF-O-CF_2-CF_2-CF=CF_2$$ (m24-1), $$CF_2=CF-O-CF_2-CF(CF_3)-CF=CF_2$$ (m24-2), $$CF_2=CF-O-CF(CF_3)-CF_2-CF=CF_2$$ (m24-3).

Further, as another branched polymer, a branched multi-segmented copolymer may be mentioned wherein at least one linear molecular chain made of a segment (B) having units (3) based on a monomer (m3) having the after-described ionic precursor group, is bonded to a terminal of a branched molecular chain made of a segment (A) comprising units (m1) based on a monomer (m1) having an iodine atom, and units (m2) based on either one or both of a monomer (m2) having an alicyclic structure and a monomer (m2') capable of forming an alicyclic group by cyclopolymerization. The segment (A) and the segment (B) may contain units (m4) based on a monomer (m4) other than the monomer (m1), the monomer (m2), the monomer (m2') and the monomer (m3).

Here, the "ionic group" is a group having H+, a monovalent metal cation, an ammonium ion, etc. The monomer (m1), the monomer (m2), the monomer (m2') and the monomer (m4) do not have an ionic group or a precursor group thereof.

At a terminal of the segment (B) in the branched multi-segmented copolymer, there is a group (1 i) or group (2i) in which an iodine atom is bonded. Some of groups (1 i) or groups (2i) contained in the segment (A) may remain.

The branched multi-segmented copolymer may be used as an electrolyte material for a fuel cell, etc., after precursor groups (groups such as —$SO_2F$ groups that can be converted to ionic groups by known treatment such as hydrolysis or treatment for conversion to an acid form) for ionic groups are converted to ionic groups (sulfonic acid groups (—$SO_3^-$ $H^+$ groups)), but if groups (1i) or groups (2i) remain in the polymer, they may be influential over the performance of the fuel cell.

The monomer (m1) and the monomer (m2) in the branched multi-segmented copolymer are the same as described above.

Monomer (m3):

A monomer (m3) is a monomer having a precursor group for an ionic group. As such a monomer (m3), from the viewpoint of durability as an electrolyte material, particularly as an electrolyte material for a fuel cell, a perfluoromonomer is preferred.

The monomer (m3) may, for example, be a monomer (m3-1) having one precursor group, a monomer (m3-2) having two precursor groups, etc.

Monomer (m3-1):

As the monomer (m3-1), a monomer (m31) is preferred from such a viewpoint that it is thereby easy to produce a branched polymer, and that industrial practice will be easy.

$$CF_2=CF(CF_2)_pOCF_2-CFY^1-Q^3-SO_2F$$ (m31).

$Q^3$ is a single bond or a perfluoroalkylene group which may have an etheric oxygen atom.

In a case where the perfluoroalkylene group for $Q^3$ has an etheric oxygen atom, the number of the oxygen atoms may be one or may be two or more. Further, such an oxygen atom may be inserted between carbon-carbon atoms in the perfluoroalkylene group, or may be present at the terminal on the $CFY^1$ side.

The perfluoroalkylene group may be linear or branched and is preferably linear. The number of carbon atoms in the perfluoroalkylene group is preferably from 1 to 6, more preferably from 1 to 4.

$Y^1$ is a fluorine atom or a monovalent perfluoro-organic group. As $Y^1$, a fluorine atom or a trifluoromethyl group is preferred.

p is 0 or 1.

As the monomer (m31), from such a viewpoint that it is easy to produce a polymer and industrial practice is easy, monomers (m31-1) to (m31-4) are preferred.

$$CF_2=CFOCF_2CF(CF_3)OCF_2CF_2-SO_2F \quad \text{(m31-1)},$$

$$CF_2=CFOCF_2CF_2-SO_2F \quad \text{(m31-2)},$$

$$CF_2=CFOCF_2CF_2CF_2CF_2-SO_2F \quad \text{(m31-3)},$$

$$CF_2=CFCF_2OCF_2CF_2-SO_2F \quad \text{(m31-4)}.$$

Monomer (m3-2):

As the monomer (m3-2), the following monomer (m32) is preferred.

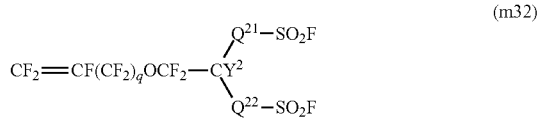

q is 0 or 1.

$Q^{21}$ is a perfluoroalkylene group which may have an etheric oxygen atom. $Q^{22}$ is a single bond or a perfluoroalkylene group which may have an etheric oxygen atom.

In a case where the perfluoroalkylene group for $Q^{21}$ or $Q^{22}$ has an etheric oxygen atom, the number of the oxygen atoms may be one or may be two or more. Further, such an oxygen atom may be inserted between carbon-carbon atoms in the perfluoroalkylene group, or may be present at the terminal on the $CY^2$ side. The perfluoroalkylene group may be linear or branched and is preferably linear. The number of carbon atoms in the perfluoroalkylene group is preferably from 1 to 6, more preferably from 1 to 4.

It is preferred that at least one of $Q^{21}$ and $Q^{22}$ is a $C_{1-6}$ perfluoroalkylene group having an etheric oxygen atom at the terminal on the $CY^2$ side.

$Y^2$ is a fluorine atom or a monovalent perfluoro-organic group. $Y^2$ is preferably a fluorine atom or a $C_{1-6}$ linear perfluoroalkyl group which may have an etheric oxygen atom.

As the monomer (m32), from such a viewpoint that it is easy to produce a polymer, and industrial practice is easy, monomers (m32-1) to (m32-3) are preferred, and the monomer (m32-1) is particularly preferred.

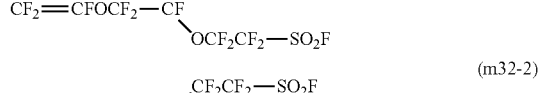

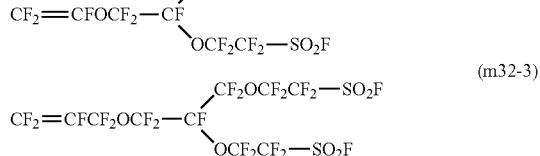

The above-described amorphous branched polymer or branched multi-segmented copolymer may contain units based on a monomer (m4).

Monomer (m4): A monomer (m4) is a monomer other than the monomer (m1), the monomer (m2), the monomer (m2') and the monomer (m3).

The monomer (m4) may, for example, be tetrafluoroethylene (TFE), chlorotrifluoroethylene, trifluoroethylene, vinylidene fluoride, vinyl fluoride, ethylene, propylene, a perfluoro α-olefin (such as hexafluoropropylene), a (perfluoroalkyl) ethylene (such as (perfluorobutyl) ethylene), a (perfluoroalkyl) propene (such as 3-perfluorooctyl-1-propene), etc. As the monomer (m4), from the viewpoint of durability, a perfluoromonomer is preferred, and TFE is more preferred.

The above-described amorphous branched polymer or branched multi-segmented copolymer is prepared by using a known conventional radical polymerization method.

(Organic Peroxide)

In the present invention, the iodine containing compound is treated by using an organic peroxide. Even if the iodine-containing compound having a group (1i) or group (2i) is treated by using an inorganic oxide or azo compound, it is difficult to thereby efficiently convert the C—I bond in the iodine-containing compound to a C—H bond.

The organic peroxide may, for example, be a dialkyl peroxide, a peroxy ketal, a diacyl peroxide, a dialkyl peroxydicarbonate, a peroxy ester, a peroxy monocarbonate, a bis(fluoroacyl) peroxide, a bis(chlorofluoroacyl) peroxide, a peroxy ester, etc.

These organic peroxides include, for example, a dialkyl peroxide such as di-t-butyl peroxide, perfluoro-di-t-butyl peroxide, t-butyl cumyl peroxide, dicumyl peroxide, etc.; a peroxy ketal such as 1,1-bis(t-butylperoxy)-3,3,5-trimethylcyclohexane, 1,1-bis(t-butylperoxy) cyclohexane, 2,2-bis(4,4-di-t-butyl peroxy cyclohexyl) propane, 2,2-bis(t-butylperoxy) butane, etc.; a diacyl peroxide such as isobutyryl peroxide, acetyl peroxide, 3,3,5-trimethyl hexanoyl peroxide, lauroyl peroxide, benzoyl peroxide, a fluorine-containing diacyl peroxide such as $(Z(CF_2)_pCOO)_2$ (wherein Z is a hydrogen atom, a fluorine atom or a chlorine atom, and p is an integer of from 1 to 10), perfluoropropyl diacyl peroxide, etc.; a dialkyl peroxydicarbonate such as di-n-propyl peroxydicarbonate, diisopropyl peroxydicarbonate, di-2-ethylhexyl peroxydicarbonate, di-2-ethoxyethyl peroxydicarbonate, di-methoxybutyl peroxydicarbonate, etc.; a peroxy ester such as cumyl peroxy neodecanate, 1,1,3,3-tetramethylbutyl peroxy neodecanate, t-hexyl peroxy neodecanate, t-amyl peroxy neodecanate, t-butyl peroxy neodecanate, t-butyl peroxy neooctanate, t-butyl peroxy neohexanate, t-butyl peroxypivalate, t-butyl-2-ethylhexanate, t-butyl peroxy isobutyrate, t-butyl peroxy laurate, t-butyl peroxy-2-ethylhexanate, t-butyl peroxy benzoate, t-butyl peroxy acetate, etc.; a peroxy monocarbonate such as t-butyl peroxy isopropyl monocarbonate, t-butyl peroxy allyl monocarbonate, etc.

The 10-hour half-life temperature of the organic peroxide is preferably from 10° C. to 150° C., more preferably from 15° C. to 120° C., further preferably from 20° C. to 80° C. When the half-life temperature is within the above range, there is an advantage that it is possible to easily control the reaction rate. In the present specification, the 10-hour half-life temperature is a temperature at which at a concentration of 0.1 mol/L in benzene, upon expiration of 10 hours, the concentration of the organic peroxide becomes to be a half, and it is one of indices showing the thermal properties.

In the present invention, the organic peroxide is preferably e.g. diisopropyl peroxydicarbonate or t-butyl peroxypivalate, for such a reason that it is thereby easy to control of the reaction temperature.

The total number of moles of the organic peroxide is preferably from 0.0005 to 5 times to the total number of moles of iodine atoms in the iodine-containing compound. When it is at least 0.0005 times, the conversion in the reaction will not be too low, such being practical. When it is at most 5 times, it will not be required to add the organic peroxide more than necessary, such being preferred from the viewpoint of safety. It is more preferably from 0.005 to 2 times, further preferably from 0.01 to 1 times, particularly preferably from 0.02 to 0.5 times. Further, the concentration of the organic peroxide in the reaction liquid is, in order to carry out the reaction safely, preferably at most 5 mass %, more preferably at most 1 mass %.

Heretofore (e.g. in Patent Document 1), a carbon-iodine bond was considered to be cleaved by a radical initiator, and therefore, in order to efficiently convert a C—I bond in an iodine-containing compound to a C—H bond by an organic peroxide, it was considered necessary to use a large amount of the peroxide. It was considered that if isopentane, toluene or the like was permitted to be present, a hydrogen atom would be withdrawn for stabilization, but there was no experimental example for combination with an organic peroxide, and there was no finding about the amount of an organic peroxide required in the case of adding such a hydrocarbon compound. In an experiment in a Comparative Example of the present invention, even when toluene was added, a C—I bond was never effectively converted to a C—H bond. The present inventors have found that when a compound having a specific hydrocarbon structure which will be described later, is used, the reaction will effectively proceed even if the amount of an organic peroxide is less than heretofore. Even by an organic peroxide in the number of moles considerably less than the number of moles of iodine atoms in the iodine-containing compound, the reaction will efficiently proceed. There has been no knowledge or suggestion that the reaction will efficiently proceed even under such conditions. Heretofore, a radical formed from the organic peroxide was believed to withdraw an iodine atom from the iodine-containing compound, and therefore, there has been no attempt made to conduct a reaction to convert a C—I bond to a C—H bond by an organic peroxide in a less number of moles than the number of moles of iodine atoms. Such a reaction that a radical formed as a result of withdrawal of an iodine atom from an iodine-containing compound, will withdraw a hydrogen atom from the above-mentioned compound having a specific hydrocarbon structure, and by a radical thereby formed, an iodine atom is withdrawn from the iodine-containing compound, is repeated, whereby C—I bonds are considered to be efficiently converted to C—H bonds.

(Hydrogen-Containing Compound)

In the present invention, the iodine-containing compound is treated by using, as a chain transfer agent, a hydrogen-containing compound having a group represented by —CHR$^1$—CHR$^2$—CHR$^3$— (R$^1$, R$^2$ and R$^3$ are each independently a hydrogen atom or an alkyl group). Even if the iodine-containing compound having a group (1i) or group (2i) is treated by using e.g. methanol or toluene as a chain transfer agent, it is difficult to effectively convert a C—I bond in the iodine-containing compound to a C—H bond.

As the above hydrogen-containing compound, a chain saturated hydrocarbon (an alkane) or a cyclic saturated hydrocarbon (a cycloalkane) is preferably used, but it may be a compound having an ether bond or other functional groups. Further, the above hydrogen-containing compound may be linear or branched. An alkane or a cycloalkane is preferred, since it is easy to handle, and it is highly reactive and less likely to cause side reactions.

As the alkane, n-pentane, 2-methylbutane, n-hexane, 2-methylpentane, 2,2-dimethylbutane, 2,3-dimethylbutane, n-heptane, 2-methylhexane, 3-methylhexane, 2,4-dimethylpentane, n-octane, 2-methylheptane, 3-methylheptane, 4-methylheptane, 2,2-dimethylhexane, 2,5-dimethylhexane, 3,3-dimethylhexane, 2-methyl-3-ethylpentane, 3-methyl-3-ethylpentane, 2,3,3-trimethylpentane, 2,3,4-trimethylpentane, 2,2,3-trimethylpentane, 2-methylheptane, 2,2,4-trimethylpentane, n-nonane, 2,2,5-trimethylhexane, n-decane, n-dodecane, etc. may be mentioned. Among them, n-pentane, 2-methylbutane, n-hexane, 2-methylpentane or n-heptane is preferred.

As the cycloalkane, cyclopentane, methylcyclopentane, cyclohexane, methylcyclohexane, ethylcyclohexane, bicyclohexane, etc. may be mentioned. Among them, cyclopentane or cyclohexane is preferred.

The total number of moles of the hydrogen-containing compound is preferably from 2 to 500 times to the total number of moles of all iodine atoms in the iodine-containing compound. When the amount of the hydrogen-containing compound is at least 2 times, the hydrogen-withdrawing reaction tends to easily occur, and the reaction yield will be improved. Further, when the amount of the hydrogen-containing compound is at most 500 times, the solubility of the iodine-containing compound containing fluorine will be good, or the concentration of the iodine-containing compound will be less likely to become too small. Particularly, it is more preferably from 5 to 300 times, more preferably from 10 to 100 times.

(Fluorine-Containing Solvent)

In the present invention, it is preferred that the iodine-containing compound is treated as dissolved or dispersed in a fluorine-containing solvent.

The fluorine-containing solvent may, for example, be a perfluorocarbon, a hydrochlorofluorocarbon, a hydrofluorocarbon or a hydrofluoroether.

The perfluorocarbon may, for example, be n-perfluorohexane, n-perfluoroheptane, perfluorocyclobutane, perfluorocyclohexane, perfluorobenzene, etc.

The hydrochlorofluorocarbon may, for example, be 2,2-dichloro-1,1,1-trifluoroethane, 1,1-dichloro-1-fluoroethane, 1,1-dichloro-2,2,3,3,3-pentafluoropropane, 1,3-dichloro-1,1,2,2,3-pentafluoropropane, etc.

The hydrofluorocarbon may, for example, be 1,1,2,2-tetrafluorocyclobutane, $CF_3CF_2CH_2CH_3$, $CF_3CHF(CF_2)_3F$, $CF_3(CF_2)_4H$, $CF_3CF_2CHF(CF_2)_2F$, $CF_3(CHF)_2(CF_2)_2F$, $CHF_2CHF(CF_2)_3F$, $CF_3(CF_2)_5H$, $CF_3CH(CF_3)(CF_2)_3F$, $CF_3CF(CF_3)CHF(CF_2)_2F$, $CF_3$ $CF(CF_3)(CHF)_2$ $CF_3$, $CF_3CH(CF_3)CHF(CF_2)_2F$, $CF_3$ $(CF_2)_3$ $(CH_2)_2H$, etc.

The hydrofluoroether may, for example, be $CF_3CH_2O(CF_2)_2H$, $CHF_2$ $CF_2CH_2O(CF_2)_2H$, $CH_3O(CF_2)_4H$, $CH_3OCF_2CF(CF_3)_2$, $CF_3CHFCF_2OCF_3$, etc.

Among them, preferred is a solvent which is compatible with both the iodine-containing compound containing fluorine, as the reactive substrate, and the hydrogen-containing compound to be added, and, for example, 1,3-dichloro-1,1,2,2,3-pentafluoropropane is preferred.

(Treating Conditions)

In a solution of the fluorine-containing solvent, the concentration of the iodine-containing compound is preferably from 0.1 to 50 mass % to the reaction liquid. From the viewpoint of productivity, it is preferably at least 0.1 mass %, and with a view to preventing abrupt heat generation at the initiation of the reaction, it is preferably at most 50 mass %. It is more preferably from 1 to 30 mass %.

In a solution of the fluorine-containing solvent, the concentration of the hydrogen-containing compound is preferably from 0.1 to 30 mass % to the reaction liquid. When it is at least 0.1 mass %, it is possible to secure a suitable reaction rate. In a case where the iodine-containing compound is freely miscible with the hydrogen-containing compound, the hydrogen-containing compound may be used also as a solvent, but with a view to securing compatibility with the iodine-containing compound containing fluorine, it is preferably at most 30 mass %. It is more preferably from 1 to 20 mass %.

In the present invention, in the deiodinating treatment of the iodine-containing compound, it is preferred to conduct heating treatment for securing the decomposition temperature of the organic peroxide and for carrying out more efficient treatment. The heating temperature at that time is preferably between T° C. and T+80° C., more preferably between T+10° C. and T+50° C., where T° C. is the 10-hour half-life temperature of the organic peroxide, and from the viewpoint of the operational efficiency, it is preferred that the heat treatment is conducted at a temperature of from 50° C. to 150° C. Further, the heating time is preferably from 1 to 24 hours. Since a reaction involving rapid decomposition of the organic peroxide is dangerous, it is preferred to carry out the reaction by taking a time for at least one hour. Further, from the viewpoint of productivity, it is preferred that the heating time is within 24 hours.

(Fluorine-Containing Compound)

By the production method of the present invention, it is possible to obtain a fluorine-containing compound having the iodine atom content reduced than the iodine-containing compound. The fluorine-containing compound may have a group represented by the formula (1 h) or a group represented by the formula (2h).

—CFRf—H   Formula (1h)

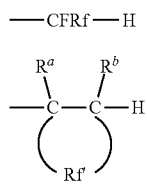

Formula (2h)

In the formula (1h), Rf is the same as described in the formula (1i).

In the formula (2h), Rf', $R^a$ and $R^b$ are the same as described in the formula (2i).

By the deiodinating treatment, the group (1i) in the iodine-containing compound can be converted to the group (1h), and the group (2i) in the iodine-containing compound can be converted to the group (2h).

In the production method of the present invention, by the deiodinating treatment, the iodine atom content in the obtainable fluorine-containing compound may be made to be at most 10% of the iodine atom content in the iodine-containing compound before the treatment. That is, as between before and after the deiodinating treatment, it is possible to remove at least 90% of iodine atoms forming all C—I bonds subjected to the reaction. In a case where the iodine-containing compound is a polymer, it is possible to readily reduce the iodine atom content in the polymer to at most 10% of the original value. For example, in the case of a polymer wherein the iodine atom content is 1 mass %, it is possible to obtain a polymer wherein the iodine atom content is reduced to at most 0.1 mass %. By the present invention, the iodine atom content in the fluorine-containing compound to be obtained, can be made to be more preferably at most 5%, further preferably to at most 3%, of the iodine atom content of the iodine-containing compound.

EXAMPLES

In the following Examples, Ex. 1 to 8, 10, 12 to 15, 21 to 26 and 30 are Examples of the present invention, and Ex. 9, 11 and 27 to 29 are Comparative Examples.

(Iodine-Containing Compounds)

PHVE-I: $CF_3CF_2CF_2OCF(CF_3)CF_2OCF_2CF_2$—I (Monomer (m1))

8IVE: $CF_2$=$CFOCF_2\ CF(CF_3)OCF_2\ CF_2$—I   (m1-1)

(Monomer (m2))

PDD:

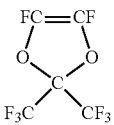

(m21-1)

(Monomer (m2'))

BVE: $CF_2$=$CF$—O—$CF_2$—$CF_2$—$CF$=$CF_2$   (m24-1)

(Monomer (m3))

PSVE:

$CF_2$=$CFOCF_2CF(CF_3)OCF_2CF_2$—$SO_2F$   (m31-1)

BSVE-2E:

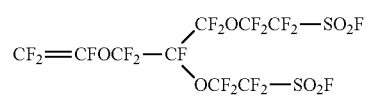

(m32-1)

(Monomer (m4))

TFE: $CF_2$=$CF_2$   (m4-1)

(Organic Peroxides)

IPP: diisopropyl peroxydicarbonate

PBPV: t-butyl peroxypivalate (Solvents)

HFC-52-13p: $CF_3(CF_2)_5H$,

HCFC-141b: $CH_3CCl_2F$,

HCFC-225cb: $CClF_2CF_2CHClF$,

HCFC-225: mixture of $CClF_2\ CF_2CHClF$ and $CF_3CF_2CHCl_2$.

[Synthesis of 8IVE (m1-1)]

8IVE (m1-1) was synthesized in the same manner as the method described in Huaxue Xuebao, Vol. 47, No. 7, 1989, pp. 720-723.

[Synthesis Example for Branched Polymer (1)]

A branched polymer (1) having units based on 8IVE (m1-1) and units based on BVE (m24-1) was synthesized as follows.

Into a Hastelloy autoclave having an internal capacity of 120 mL, 3.67 g (7.5 mmol) of 8IVE was charged. A liquid having 1.546 g (7.5 mmol) of IPP dissolved in about 15 g of HFC-52-13p and 18.77 g (67.5 mmol) of BVE were added, and finally HFC-52-13p was added. The total amount of HFC-52-13p added, was 44.01 g. Using liquid nitrogen, freeze/degassing was repeated twice to return the temperature to approximately 0° C., and then, nitrogen gas was introduced until 0.3 MPaG. The autoclave was set in a water bath, followed by stirring for 4 hours while maintaining the internal temperature at 45° C. Then, the temperature was raised to 55° C. over a period of 10 minutes, followed by stirring for 1 hour. Further, the temperature was raised to 65° C. over 10 minutes, followed by stirring for 1 hour, whereupon the temperature was raised to 70° C. over a period of 5 minutes, followed by stirring for one hour. Then, the autoclave was immersed in ice water and cooled to at most 20° C., to terminate the reaction.

The reaction liquid was transferred to a beaker from the autoclave, and about 110 g of HFC-52-13p was added. About 110 g of n-hexane was added, followed by stirring and being left overnight. The content of the beaker was transferred to an eggplant flask, and the solvent was distilled off by an evaporator, followed by vacuum drying at 60° C. for about 200 hours, to obtain 20.65 g of a solid (a branched polymer (1)). The mass average molecular weight calculated as polymethyl methacrylate measured by GPC was 8,700.

The branched polymer (1) was dissolved in perfluorobenzene, and $^{19}$F-NMR (the chemical shift of perfluorobenzene was set to be −162.7 ppm, the same applies hereinafter) was measured, whereby the ratio of the number of terminals of BVE units bonded to iodine atoms, to the number of —OCF$_2$CF$_2$—I groups based on 8IVE units with iodine atoms undissociated, was found to be 29:71 from the ratio of the peaks at from −44 to −54 ppm to the peak in the vicinity of −62 ppm, and thus, it was confirmed that this polymer contained branched molecular chains. The iodine atom content obtained by the elemental analysis was 3.4 mass %, and from this value, the molar ratio (8IVE/BVE) of units derived from 8IVE (m1-1) to units derived from BVE (m24-1) was calculated to be 1/12.

[Synthesis Example for Branched Multi-Segmented Copolymer (2)]

A branched multi-segmented copolymer (2) comprising a segment having units based on 8IVE (m1-1) and units based on PDD (m21-1), and a segment having units based on TFE (m4-1) and units based on BSVE-2E (m32-1), was synthesized as follows.

In a Hastelloy autoclave having an internal capacity of 230 mL, 5.72 g (11.7 mmol) of 8IVE was charged. A liquid having 0.241 g (1.17 mmol) of IPP dissolved in 5 g of HCFC-225cb and 25.63 g (105.0 mmol) of PDD were added, and finally HCFC-225cb was added. The total amount of HCFC-225cb added, was 118.42 g. Using liquid nitrogen, freeze/degassing was repeated twice, to return the temperature to about 0° C., and then, nitrogen gas was introduced until 0.3 MPaG (G denotes gauge pressure, the same applies hereinafter). The autoclave was set in a water bath, followed by stirring for 8 hours while maintaining the internal temperature at 45° C. After the stirring, the autoclave was immersed in ice water and cooled to at most 20° C. to terminate the reaction.

The jelly-like product was transferred to a beaker from the autoclave, and HCFC-225cb was added. The total amount was 214 g. After stirring for 5 minutes by a magnetic stirrer, 261 g of n-hexane was added to coagulate the polymer, followed by stirring continuously for 30 minutes. Vacuum filtration was conducted, and the obtained polymer was washed with n-hexane. The polymer was returned to the beaker, and HCFC-225cb was added to bring the total amount to be 214 g, followed by stirring for 5 minutes. 261 g of n-hexane was added to coagulate the polymer, followed by stirring for 30 minutes. Vacuum filtration was conducted, followed by washing with n-hexane, and then, again HCFC-225cb was added and stirred in the same manner, followed by agglomeration with n-hexane, filtration and washing with n-hexane. Then, drying was conducted in a vacuum oven at 60° C. to a constant weight, to obtain 23.75 g of a white powdery polymer (2').

With respect to the polymer (2'), the content of iodine atoms was examined by the elemental analysis and found to be 2.8 mass %. From this value, the molar ratio (8IVE/PDD) of units derived from 8IVE (m1-1) to units derived from PDD (m21-1) in the polymer (2') was calculated to be 1/17 (5.6/94.4). The mass average molecular weight of the polymer (2') calculated as polymethyl methacrylate obtained by GPC was 18,700. The polymer (2') was dissolved in perfluorobenzene, and $^{19}$F-NMR was measured, whereby it was found that units derived from PDD bonded to iodine atoms were present and the polymer (2') was confirmed to have branched structures. The ratio of units derived from PDD to which iodine atoms were bonded, to units derived from 8IVE where iodine atoms were not dissociated, was found to be 46:54 from the ratio of the peaks at from −42 to −47 ppm to the peak in the vicinity of −62 ppm in $^{19}$F-NMR (solvent: perfluorobenzene).

Into a Hastelloy autoclave having an internal capacity of 230 mL, 6.99 g of the polymer (2') and 260.32 g of BSVE-2E, were charged, and the autoclave was closed, whereupon the gas phase was replaced with nitrogen. The temperature was raised to 40° C., followed by stirring for 12 hours to dissolve the polymer (2'). After cooling to room temperature, 18.3 mg of IPP dissolved in 1.73 g of HFC-52-13p was added, and by using liquid nitrogen, freeze/degassing was repeated twice. While raising the temperature, TFE was introduced continuously, and the temperature and pressure were held constant at a temperature 40° C. under a pressure of 0.50 MPaG. Upon expiration of 10 minutes after the temperature became constant at 40° C., consumption of TFE began. Upon expiration of 4.3 hours after the TFE feed amount reached 2.37 g under the constant pressure, the autoclave was cooled to 10° C. TFE in the autoclave was purged to terminate the reaction.

After the product was diluted with 15 g of HCFC-225, 200 g of HCFC-141b was added, to precipitate the polymer, followed by filtration. The polymer was dissolved again in 150 g of HCFC-225 and precipitated by addition of 50 g of n-hexane and 140 g of HCFC-141 b, followed by filtration. The operation of dissolution and precipitation was carried out again by using the same amount of the solvent. Then, the polymer was dried at 80° C. under reduced pressure overnight, to obtain 13.3 g of a copolymer (2) being a branched multi-segmented copolymer comprising a precursor of a segment (B) consisting of units derived from TFE (m4-1) and units derived from BSVE-2E (m32-1), and a segment (A) consisting of units derived from PDD (m21-1) and units derived from 8IVE (m1-1).

The molar ratio of the units in the segment (B) obtained from $^{19}$F-NMR (solvent: perfluorobenzene) of the copolymer (2), was TFE/BSVE-2E=78.9/21.1, and the ion exchange capacity of the segment was calculated to be 2.00 meq/g dry resin. The ion exchange capacity of the copolymer (2) obtained by a titration method was 1.22 meq/g dry resin.

The peak of the measured GPC chart was one, and the mass average molecular weight of the copolymer (2) calculated as polymethyl methacrylate was 101,000.

[Synthesis Example for Branched Polymer (3)]

Copolymerization of 8IVE and PDD was carried out in the same manner as the above synthesis of the polymer (2'), to obtain a polymer (3) having an iodine content of 2.2 mass % and containing a branched molecular chain wherein the molar ratio of 8IVE to PDD was 1:22. The mass average molecular weight of the polymer (3) calculated as polymethyl methacrylate obtained by GPC was 18,900.

[Synthesis Example for Branched Multi-Segmented Copolymer (4)]

By the same operation as the synthesis for the branched multi-segmented copolymer (2), a branched polymer was synthesized which had a segment made of a copolymer of 8IVE and PDD (the molar ratio of the units was 8IVE/PDD=5.0/95.0) and a segment made of a copolymer of TFE and BSVE-2E (the molar ratio of the units was TFE/BSVE-2E=79.1/20.9). The ion exchange capacity was 1.42 meq/g dry resin.

Ex. 1

Into a Hastelloy autoclave having an internal capacity of 34 mL, PHVE-I, IPP (diisopropyl peroxydicarbonate) being an organic peroxide as the radical generating source, n-hexane as the hydrogen-containing compound, HCFC-225cb (1,3-dichloro-1,1,2,2,3-pentafluoropropane) as a solvent, were added. Using liquid nitrogen, freeze/degassing was repeated twice to return the temperature to about 0° C., and then nitrogen gas was introduced until 0.3 MPaG, followed by heat treatment at 70° C. for 7 hours.

In the above charging, the total amount of the charged liquid was 18 g, and the concentration of PHVE-I was made to be 5 mass %. The ratio of the total number of moles of the organic peroxide (IPP) to the total number of moles of iodine atoms in PHVE-I was made to be 2. The concentration of the hydrogen-containing compound (hexane) was made to be 10 mass %. At that time, the ratio of the total number of moles of the hydrogen-containing compound (hexane) to the total number of moles of iodine atoms in PHVE-I was 13.4.

The yield of $CF_3CF_2CF_2OCF(CF_3)CF_2OCF_2CF_2$—H (hereinafter referred to as "PHVE-H") obtained, was 96.8%.

Ex. 2 to 11

Heat treatment was conducted in the same manner as in Ex. 1 except that the following conditions were changed as shown in Table 1. The yield of the obtained PHVE-H is shown in Table 1.

The concentration of PHVE-I in the HCFC-225cb solution.

The type of the radical-generating source (organic peroxide), and the ratio of the total number of moles of the radical generating source to the total number of moles of iodine atoms in PHVE-I.

The type of the chain transfer agent, the total number of moles of the chain transfer agent to the total number of moles of iodine atoms in PHVE-I, and the concentration of the chain transfer agent in the HCFC-225cb solution.

Further, In Ex. 8, the reaction temperature was made to be 60° C., and in Ex. 11, the reaction temperature was made to be 75° C.

TABLE 1

| | PHVE-I | Radical generating source | | Chain transfer agent | | | Yield |
|---|---|---|---|---|---|---|---|
| | Concentration | | | | | Concentration | |
| Ex. | (mass %) | Type | Ratio | Type | Ratio | (mass %) | (%) |
| 1 | 5 | IPP | 2 | n-hexane | 13.4 | 10 | 96.8 |
| 2 | 5 | IPP | 0.5 | n-hexane | 13.4 | 10 | 96.9 |
| 3 | 5 | IPP | 0.1 | n-hexane | 13.4 | 10 | 96.6 |
| 4 | 5 | IPP | 0.1 | n-hexane | 1.0 | 0.74 | 28.5 |
| 5 | 5 | IPP | 0.01 | n-hexane | 13.4 | 10 | 74.7 |
| 6 | 5 | IPP | 0.002 | n-hexane | 13.4 | 10 | 29.8 |
| 7 | 0.5 | IPP | 0.1 | n-hexane | 13.4 | 1 | 97.2 |
| 8 | 5 | IPP | 0.1 | n-hexane | 13.4 | 10 | 96.7 |
| 9 | 5 | IPP | 0.1 | Toluene | 12.6 | 10 | Not reacted |
| 10 | 5 | PBPV | 0.5 | n-hexane | 13.4 | 10 | 94.3 |
| 11 | 5 | AIBN | 0.1 | n-hexane | 13.4 | 10 | Not reacted |

Ex. 12

The reaction was conducted under the same conditions as in Ex. 3, except that instead of PHVE-I, $CF_3CF_2CF_2OCF(CF_3)CF_2OCF(CF_3)$—I was used. The obtained product was $CF_3CF_2CF_2OCF(CF_3)CF_2OCF(CF_3)$—H, and the yield was 98.1%.

Ex. 13

In a stainless steel autoclave having an internal capacity of 110 mL, IPP as the organic peroxide and n-hexane as the hydrogen-containing compound were added to a solution having 1.35 g of the branched polymer (1) dissolved in HCFC-225cb. Using liquid nitrogen, freeze/degassing was repeated twice, to return the temperature to about 0° C., and then nitrogen gas was introduced until 0.3 MPaG, followed by stirring at 70° C. for 7 hours.

In the above reaction, the concentration of the branched polymer (1) to HCFC-225cb was made to be 2 mass %. The ratio of the total number of moles of the organic peroxide (IPP) to the total number of moles of iodine atoms in the branched polymer (1) was made to be 2. The concentration of the hydrogen-containing compound (n-hexane) to the total charged weight was made to be 1 mass %. At that time, the ratio of the total number of moles of the hydrogen-containing compound to the total number of moles of iodine atoms in the branched polymer (1) was 22.

With respect to the reaction product, using a perfluorobenzene solvent, $^{19}$F-NMR measurement was conducted, whereby it was found that the peaks due to —$CF_2$—I bonds had disappeared, and $^1$H-NMR measurement was conducted whereby a peak (triplet) due to a H atom in —$CF_2$—H was observed at 6.0 ppm.

Ex. 14

The treatment of the branched polymer (1) was carried out in the same manner as in Ex. 13, except that the ratio of the total number of moles of the organic peroxide (IPP) to the total number of moles of iodine atoms in the branched polymer (1) was made to be 0.5.

With respect to the reaction product, using a perfluorobenzene solvent, $^{19}$F-NMR measurement was conducted, whereby it was found that the peaks due to —$CF_2$—I bonds had disappeared, and $^1$H-NMR measurement was conducted whereby a peak (triplet) due to a H atom in —CF$_2$—H was observed at 6.0 ppm.

Ex. 15

In Ex. 13, the object to be treated was changed from the branched polymer (1) to the branched polymer (3). Further, the concentration of the branched polymer (3) to HCFC-225cb was changed to be 1.5 mass %. The ratio of the total number of moles of the organic peroxide (IPP) to the total number of moles of iodine atoms in the branched polymer (3) was made to be 0.5. The concentration of the hydrogen-containing compound (n-hexane) to the total charged weight was made to be 1 mass %. At that time, the total number of moles of the hydrogen containing compound to the total number of moles of iodine atoms in the branched polymer (1) was 45. The treatment was carried out by setting other conditions in the same manner as in Ex. 13.

With respect to the reaction product, using a perfluorobenzene solvent, $^{19}$F-NMR measurement was conducted, whereby it was found that the peaks at from −42 to −47 ppm and the peak in the vicinity of −62 ppm due to fluorine atoms bonded to the same carbon atom as the iodine atom had disappeared. $^1$H-NMR was measured whereby a triplet due to a H atom in —CF$_2$—H was observed at 6.0 ppm, and a doublet due to a H atom based on the following structure was observed at 6.6 ppm.

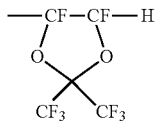

Ex. 21

With respect to the branched multi-segmented copolymer (2), the iodine atom content was measured by the elemental analysis and found to be 0.9 mass %.

In a Hastelloy autoclave having an internal capacity of 34 mL, IPP as the organic peroxide, n-hexane as the hydrogen-containing compound and additional HCFC-225cb were added to a solution having 0.45 g of the copolymer (2) dissolved in HCFC-225cb at a concentration of 3 mass %. Using liquid nitrogen, freeze/degassing was repeated twice to return the temperature to about 0° C., and then, nitrogen gas was introduced until 0.3 MPaG, followed by heat treatment at 70° C. for 7 hours.

In the above reaction, the concentration of the copolymer (2) to the total charged amount was made to be 2 mass %. The ratio of the total number of moles of the organic peroxide to the total number of moles of iodine atoms in the copolymer (2) was made to be 16.4. The concentration of the hydrogen-containing compound (n-hexane) to the total charged amount was made to be 1 mass %. The ratio of the total number of moles of the hydrogen-containing compound to the total number of moles of iodine atoms in the copolymer (2) was 82.

The residual iodine content in the polymer after the heat treatment was measured by the elemental analysis and found to be 0.02%.

Ex. 22 to 29

Heat treatment was carried out in the same manner as in Ex. 21, except that the following conditions were changed as shown in Table 2. The yield of the polymer after the heat treatment is shown in Table 2.

The concentration of the copolymer (2) in the total charged liquid.

The ratio of the total number of moles of the organic peroxide to the total number of moles of iodine atoms in the copolymer (2).

The type of the chain transfer agent, and the ratio of the total number of moles of the chain transfer agent to the total numbers of moles of iodine atoms in the copolymer (2).

Further, In Ex. 28, the reaction conditions were set to be such that heating at 60° C. for 5 hours, was followed by heating at 70° C. for 3 hours.

TABLE 2

| Ex. | Copolymer (2) Concentration (mass %) | Organic peroxide Type | Organic peroxide Ratio | Chain transfer agent Type | Chain transfer agent Ratio | Concentration | Iodine atom content Concentration (mass %) |
|---|---|---|---|---|---|---|---|
| 21 | 2 | IPP | 16.4 | n-hexane | 82 | 1 | 0.02 |
| 22 | 2 | IPP | 8.2 | n-hexane | 82 | 1 | 0.02 |
| 23 | 2 | IPP | 4.1 | n-hexane | 82 | 1 | 0.03 |
| 24 | 2 | IPP | 1.6 | n-hexane | 82 | 1 | 0.04 |
| 25 | 4 | IPP | 4.1 | n-hexane | 41 | 1 | 0.04 |
| 26 | 2 | IPP | 16.4 | Isohexane | 82 | 1 | 0.02 |
| 27 | 2 | IPP | 16.4 | Nil | | | 0.2 |
| 28 | 2 | IPP | 16.4 | Nil | | | 0.07 |
| 29 | 2 | IPP | 16.4 | Methanol | 220 | 1 | 0.41 |

Ex. 30

With respect to the branched multi-segmented copolymer (4), the iodine atom content was measured by the elemental analysis and found to be 0.49 mass %.

This polymer was dissolved in a HCFC-225cb solvent, and the reaction was conducted at 70° C. for 7 hours in the same manner as in Ex. 21. However, in the above reaction, the concentration of the copolymer (4) to the total charged amount was made to be 2 mass %. The ratio of the total number of moles of the organic peroxide (IPP) to the total number of moles of iodine atoms in the copolymer (4) was made to be 5.4. The concentration of the hydrogen-containing compound (n-hexane) in the total charged amount was made to be 1 mass %. The ratio of the total number of moles of the hydrogen-containing compound to the total number of moles of iodine atoms in the copolymer (4) was 150.

After the reaction, the temperature was returned to room temperature, and then, a HCFC-225cb solution of IPP (concentration 3 mass %) was added. The ratio of the total number of moles of IPP to the total number of moles of iodine atoms in the copolymer (4) originally charged, was 5.5. The same operation was again carried out to conduct the reaction at 70° C. for 7 hours. With respect to the obtained polymer, the elemental analysis was carried out, whereby iodine atoms were not detected (less than 0.01 mass %).

INDUSTRIAL APPLICABILITY

The fluorine-containing polymer compound containing fluorosulfonyl groups obtainable by the present invention is useful as an intermediate for an electrolyte material for polymer electrolyte fuel cells. Further, it may be used as an intermediate for other applications (water electrolysis, hydrogen peroxide production, ozone production, proton permselective membrane to be used for spent acid recovery, etc.; sodium chloride electrolysis, diaphragm for redox flow battery, cation exchange membrane for electrodialysis to be used for desalting or salt production, moisture-removing membrane, humidifying membrane, acid catalyst for chemical reactions, a sensor, gas separation membrane, etc.). The fluorine-containing polymer compound containing no ionic groups obtainable by the process of the present invention, is useful as insulating film for a semiconductor device or electronic circuit board, optical waveguide material, antireflection material, sealing material, water repellent, oil repellent, etc.

This application is a continuation of PCT Application No. PCT/JP2016/084325, filed on Nov. 18, 2016, which is based upon and claims the benefit of priority from Japanese Patent Application No. 2015-227178 filed on Nov. 20, 2015. The contents of those applications are incorporated herein by reference in their entireties.

What is claimed is:

1. A method for producing a fluorine-containing compound having an iodine atom content reduced than the following iodine-containing compound, which comprises subjecting an iodine-containing compound having a group represented by the following formula (1i) or a group represented by the following formula (2i), to deiodinating treatment in the presence of an organic peroxide and a hydrogen-containing compound having a group represented by the following formula (3):

—CFRf—I  Formula (1i)

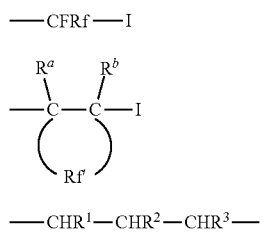  Formula (2i)

—CHR$^1$—CHR$^2$—CHR$^3$—  Formula (3)

in the formula (1i), Rf is a fluorine atom or a perfluoroalkyl group;

in the formula (2i), the ring containing Rf' is a 5- or 6-membered ring, Rf' is a perfluoroalkylene group having a linear or branched structure, which may have an etheric oxygen atom, and R$^a$ and R$^b$ are each independently a fluorine atom, a $C_{1-5}$ perfluoroalkyl group or a $C_{1-5}$ perfluoroalkoxy group, and in the formula (3), R$^1$, R$^2$ and R$^3$ are each independently a hydrogen atom or an alkyl group, wherein the fluorine-containing compound has a group represented by the following formula (1h) or a group represented by the following formula (2h):

—CFRf—H  Formula (1h)

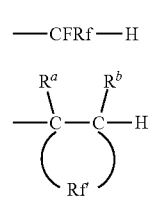  Formula (2h)

Rf in the formula (1h) and Rf', R$^a$ and R$^b$ in the formula (2h) are as defined above.

2. The method according to claim 1, wherein the iodine-containing compound is a compound represented by the following formula (4), or a compound represented by the following formula (5):

Q$^1$-CFRf-I  Formula (4)

Q$^2$-(CFRf-I)$_2$  Formula (5)

in the formula (4), Rf is a fluorine atom or a perfluoroalkyl group, and Q$^1$ is a fluorine atom or a polyfluoroalkyl group which may have an etheric oxygen atom, and in the formula (5), Rf are each independently a fluorine atom or a perfluoroalkyl group, and Q$^2$ is a polyfluoroalkylene group which may have an etheric oxygen atom.

3. The method according to claim 1, wherein the iodine-containing compound is a polymer compound which has at least one C—I bond, wherein all of hydrogen atoms bonded to carbon atoms are substituted by fluorine atoms.

4. The method according to claim 1, wherein the organic peroxide has a 10 hour half-life temperature of from 10° C. to 150° C.

5. The method according to claim 4, wherein the hydrogen-containing compound is an alkane.

6. The method according to claim 1, wherein the total number of moles of the organic peroxide is from 0.0005 to 5 times to the total number of moles of iodine atoms in the iodine-containing compound.

7. The method according to claim 1, wherein the total number of moles of the hydrogen-containing compound is from 5 to 500 times to the total number of moles of iodine atoms in the iodine-containing compound.

8. The method according to claim 1, wherein the iodine-containing compound is treated in a fluorine-containing solvent.

9. The method according to claim 1, wherein the iodine-containing compound is from 0.1 to 50 mass % of a reaction liquid for said deiodinating treatment.

10. The method according to claim 1, wherein the hydrogen-containing compound is from 0.1 to 30 mass % of a reaction liquid for said deiodinating treatment.

11. The method according to claim 1, wherein said deiodinating treatment is at a temperature between T° C. and T+80° C., where T° C. is the 10-hour half-life temperature of the organic peroxide.

12. The method according to claim 1, wherein the iodine atom content in the fluorine-containing compound is at most 10% of the iodine atom content in the iodine-containing compound.

* * * * *